United States Patent [19]
Hanley

[11] Patent Number: 5,910,495
[45] Date of Patent: Jun. 8, 1999

[54] USE OF 1,5-BENZO[B]1,4-DIAZEPINES TO CONTROL GASTRIC EMPTYING

[75] Inventor: Rochelle Marie Hanley, Chapel Hill, N.C.

[73] Assignee: Glaxo Wellcome Inc., Research Triangle Park, N.C.

[21] Appl. No.: 08/817,727

[22] PCT Filed: Oct. 13, 1995

[86] PCT No.: PCT/US95/12830

§ 371 Date: Apr. 14, 1997

§ 102(e) Date: Apr. 14, 1997

[87] PCT Pub. No.: WO96/11691

PCT Pub. Date: Apr. 25, 1996

[30] Foreign Application Priority Data

Oct. 14, 1994 [GB] United Kingdom ............ 9420747

[51] Int. Cl.$^6$ .................. A01N 43/62; C07D 243/12
[52] U.S. Cl. ............................. 514/221; 540/518
[58] Field of Search ................ 514/221; 540/518

[56] References Cited

U.S. PATENT DOCUMENTS

| | | | |
|---|---|---|---|
| 4,988,692 | 1/1991 | Gasc et al. | 514/221 |
| 5,187,154 | 2/1993 | Phillips et al. | 514/12 |
| 5,585,376 | 12/1996 | Finch et al. | 514/221 |
| 5,646,140 | 7/1997 | Sugg et al. | 517/221 |

FOREIGN PATENT DOCUMENTS

WO A 94 24149  10/1994  WIPO.

*Primary Examiner*—Mukund J. Shah
*Assistant Examiner*—Tamthom T. Ngo
*Attorney, Agent, or Firm*—Shah R. Makujina

[57] ABSTRACT

A method of controlling gastric emptying in patients having an early non-insulin-dependent diabetic condition and exhibiting rapid gastric emptying comprising the administration of an effective gastric emptying controlling amount of a compound of Formula (I)

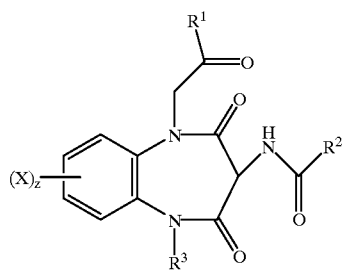

(I)

or a physiologically acceptable salt or solvate thereof.

10 Claims, No Drawings

USE OF 1,5-BENZO[B]1,4-DIAZEPINES TO CONTROL GASTRIC EMPTYING

This is a 371 application of PCT/US95/12,8230, filed on Oct. 13, 1995 which claim the priority of GB 9420797.9 filed on Oct. 14, 1994.

This invention relates to a new medical use of 1,5-benzodiazepine derivatives which exhibit CCK-A agonist activity. More particularly it relates to the use of such compounds to control gastric emptying in patients having an early non-insulin-dependent diabetic condition.

Cholecystokinins (CCK) and gastrin are structurally related peptides which exist in gastrointestinal tissue and in the central nervous system. Cholecystokinins include CCK-33, a neuropeptide of thirty-three amino acids in its originally isolated form, its carboxyl terminal octapeptide, CCK-8 (also a naturally occurring neuropeptide), and 39- and 12-amino acid forms. Gastrin occurs in 34-, 17- and 14-amino acid forms, with the minimum active sequence being the C-terminal tetrapeptide, Trp-Met-Asp-Phe-$NH_2$ (CCK-4) which is the common structural element shared by both CCK and gastrin.

CCK and gastrin are gastrointestinal hormones and neurotransmitters in the neural and peripheral systems and perform their respective biological roles by binding to particular receptors located at various sites throughout the body. There are at least two subtypes of cholecystokinin receptors termed CCK-A and CCK-B and both are found in the periphery and in the central nervous system.

The CCK-A receptor, commonly referred to as the "peripheral-type" receptor, is primarily found in the pancreas, gallbladder, ileum, pyloric sphincter and on vagal afferent nerve fibers. Type-A CCK receptors are also found in the brain in discrete regions and serve to provide a number of CNS effects. Due to the ability of CCK-8 and Type-A CCK-selective agonists to suppress food intake in several animal species, considerable interest has been generated toward the development of new substances which function as Type-A receptor-selective CCK agonists in order to serve as anorectic agents.

The CCK-B or gastrin receptors are found in peripheral neurons, gastrointestinal smooth muscle and gastrointestinal mucosa, most notably in parietal cells, ECL cells, D cells and chief cells. CCK-B receptors also predominate in the brain and have been implicated in the regulation of anxiety, arousal and the action of neuroleptic agents.

U.S. Pat. No. 4,988,692, to Gasc, et al. describes a group of 3-acylamino 1-alkyl-5-phenyl 1,5-benzodiazepine derivatives which behave as cholecystokinin antagonists to reverse or block the effects of the endogenous hormone at its receptors.

U.S. Pat. No. 4,490,304 and PTC applications No's W090/06937 and WO911/19733 describe peptide derivatives that exhibit CCK-A agonist activity. Such compounds have been disclosed for appetite regulation as well as the treatment and/or prevention of gastrointestinal disorders or disorders of the central nervous in animals and, more particularly, humans.

U.S. Pat. No. 5,187,154 which is incorporated herein by reference describes the use of the neuropeptide cholecystokinin (CCK) to control gastric emptying in patients having an early non-insulin-dependent diabetic condition and exhibiting rapid gastric emptying. Further the specification teaches that compounds which inhibit gastric emptying may be useful to alleviate or eliminate symptoms associated with early or pre-diabetes. Particular symptoms include elevated blood glucose and insulin levels, insulin resistance, increased susceptibility to infection or glycosuria while also maintaining gastric emptying within normal levels.

We have now discovered that a novel group of 3-amino 1,5-benzodiazepine compounds which exhibit agonist activity for the CCK-A receptor delay or inhibit gastric emptying and thus may be used to treat patents having non-insulin-dependent diabetic conditions and exhibiting rapid gastric emptying.

The present invention thus provides for the use of compounds of the general Formula (I)

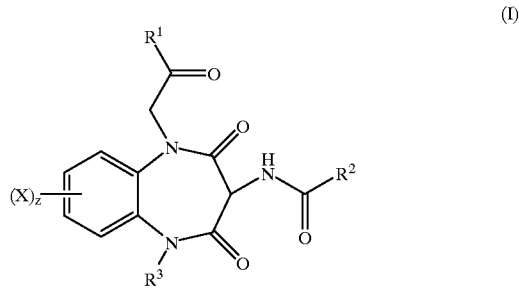

(I)

and physiologically salts and solvate thereof wherein:

X is either hydrogen, trifluoromethyl, alkyl, $C_{1-4}$alkylthio, —O($C_{1-4}$alkyl) or halogen;

$R^1$ is either Formula II or —$NR^4R^5$;

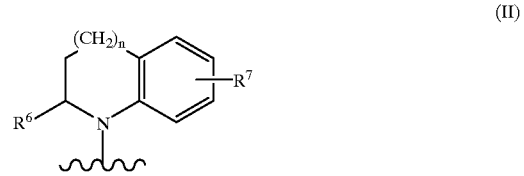

(II)

$R^2$ is either:

(1) a heterocycle linked at its 2- position and selected from pyrrole, tetrahydropyrrole, indole, benzofuran, thiophene, benzothiophene, indoline, quinoline or 4-oxobenzopyran and wherein said pyrrole, tetrahydropyrrole, indole or indoline may optionally be substituted on the ring nitrogen thereof by the group $R^8$ as defined hereunder and said indole, indoline, quinoline, benzofuran, benzothiophene or 4-oxo-benzopyran may optionally be substituted in the benzo ring thereof by the group $R^9$ as defined hereunder or (2) phenyl or phenyl mono- or disubstituted independently with halogen, hydroxy, cyano, carboxy, —O($C_{1-4}$alkyl), —O($CH_2C_6H_5$), —COO($C_{1-4}$alkyl), amino, dimethylamino, —$NHR^{10}$, 1-pyrrolidinyl or tetrazolyl; or (3) pyridine or pyridinyl mono- or disubstituted independently with halogen, methyl, hydroxy, nitro, cyano, carboxy, —O($C_{1-4}$ alkyl), —O($CH_2C_6H_5$), —COO($C_{1-4}$alkyl), amino or dimethylamino; or (4) —$NHR^{11}$ where $R^{11}$ is defined hereinunder or $R^{11}$ is 7-indazolyl containing a group $R^{10}$ at the N-1 position;

$R^3$ is hydrogen, $C_{1-6}$alkyl, $C_{3-6}$cycloalkyl, phenyl or phenyl mono- or disubstituted independently with halogen;

$R^4$ is independently $C_{3-6}$alkyl, $C_{3-6}$cycloalkyl, $C_{3-6}$alkenyl, phenyl, —($CH_2$)$_p$CN or —($CH_2$)$_p$COO ($C_{1-4}$alkyl) and $R^5$ is independently $C_{3-6}$alkyl, $C_{3-6}$cycloalkyl, $C_{3-6}$alkenyl, benzyl, phenyl or phenyl mono- or disubstituted independently with $C_{1-3}$alkyl, optionally substituted by 1 or more fluorine atoms cyano, hydroxy, dimethylamino, —O($C_{1-4}$alkyl), —O($CH_2C_6H_5$), —NH($C_{1-4}$alkyl), —COO($C_{1-4}$alkyl), —N($C_{1-4}$alkyl)$_2$ pyrrolidino, morpholino or halogen or $R^4$ is $C_{1-2}$alkyl and $R^5$ is phenyl substituted at the 2- or 4- position with chloro, methyl, methoxy or methoxycarbonyl;

$R^6$ is hydrogen or methyl;

$R^7$ is hydrogen, hydroxy, fluoro, dimethylamino, —O($C_{1-4}$alkyl) or —O($CH_2C_6H_5$);

$R^8$ is —($CH_2$)$_b$COOH;

$R^9$ is methyl, chloro, nitro, hydroxy, methoxy or —NHR$^{10}$;

$R^{10}$ is hydrogen, acetyl, $C_{-4}$alkyl, —SO$_3$H, —SO$_2$CH$_3$, —SO$_2$CF$_3$ or —SO$_2$C$_6$H$_5$, $C_{1-4}$alkoxycarbonyl;

$R^{11}$ is phenyl or phenyl mono- or disubstituted independently with fluorine, trifluoromethoxy, $C_{-4}$alkylthio, —(CH$_2$)$_c$COOH, —(CH$_2$)$_c$COO(C$_{1-4}$alkyl), —(CH$_2$)$_c$SCH$_3$, —(CH$_2$)$_c$SOCH$_3$, —(CH$_2$)$_c$SO$_2$CH$_3$, —(CH$_2$)$_c$CONH$_2$, —SCH$_2$COOH, —CONH(SO$_2$CH$_3$), —CONH(SO$_2$CF$_3$), —(CH$_2$)$_c$N(C$_{1-4}$alkyl)$_2$, (CH$_2$)$_c$NH(SO$_2$CF$_3$), —(CH$_2$)$_c$N(SO$_2$CF$_3$)(C$_{1-4}$alkyl), —(CH$_2$)$_c$SO$_2$NHCO(C$_{1-4}$alkyl), —(CH$_2$)$_c$SO$_2$N(C$_{1-4}$alkyl)CO(C$_{1-4}$alkyl), —(CH$_2$)$_c$CONHSO$_2$(C$_{1-4}$alkyl), -(CH$_2$)$_c$CON (C$_{1-4}$alkyl)SO$_2$(C$_{1-4}$alkyl), —(CH$_2$)$_c$OR$^{12}$ —(CH$_2$)$_c$NHR$^{10}$ or phenyl monosubstituted with —(CH$_2$)$_c$(tetrazolyl), —(CH$_2$)$_c$(carboxamidotetrazolyl) or —(CH$_2$)$_c$(pyrrolidinyl) or $R^{11}$ is selected from pyridine or pyridinyl mono- or disubstituted independently with halogen, methyl, hydroxy, nitro, cyano, carboxy, —O(C$_{1-4}$ alkyl), amino, dimethylamino, —NHR$^{10}$;

$R^{12}$ is hydrogen, $C_{1-6}$alkyl, $C_{3-6}$cycloalkyl, —CH$_2$C$_6$H$_5$, —CH$_2$COOH, —CH$_2$CONH$_2$, —CH$_2$CONH(C$_{1-4}$alkyl), —CH$_2$CON(C$_{1-4}$alkyl)$_2$ or

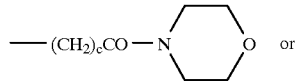

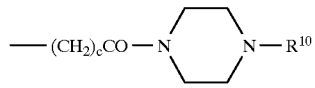

z is 1 or 2;

n is 1 or 2;

p is an integer from 1–4;

b is an integer from 0–3; and c is 0 or 1, in the manufacture of a therapeutic agent for controlling gastric emptying in patients having an early non-insulin-dependent diabetic condition and exhibiting rapid gastric emptying.

When $R^1$ represents the group of Formula (II), examples of such a group include those wherein $R^6$ is hydrogen or more particularly methyl, $R^7$ is hydrogen, hydroxyl, methoxy, or fluorine, and n is 1.

When $R^1$ represents the group NR$^4$R$^5$, examples of suitable groups include those wherein $R^4$ represent $C_{3-6}$ alkyl, such as propyl or isopropyl, cyclohexyl or phenyl and $R^5$ represents $C_{3-6}$ alkyl, benzyl or phenyl optionally substituted in the para- position by hydroxy, dimethylamino methoxy, trifluoromethyl, fluorine, pyrrolidino or morpholino. Within this group, particularly useful $R^1$ groups include those wherein $R^4$ is propyl and, more particularly, isopropyl and $R^5$ represents phenyl or phenyl substituted in the para-position by groups selected from hydroxy, methoxy dimethylamino, fluorine, or morpholino.

Examples of particularly suitable $R^1$ groups include those wherein $R^1$ is the group of Formula (II) wherein $R_6$ is methyl, n is 1 and $R^7$ is hydrogen, hydroxy, fluorine or methoxy or $R^1$ is the group NR$^4$R$^5$ wherein $R^4$ is propyl or isopropyl and $R^5$ is phenyl optionally substituted in the para position by a group selected from hydroxy, methoxy, fluoro, trifluoromethyl, dimethylamino, pyrrolidino or morpholino.

When $R^2$ represents a group selected from indole, indoline, benzofuran, benzothiophene, quinoline or 4-oxobenzopyran, the optional substituent $R^9$ is conveniently a group selected from hydrogen, methyl, methoxy, hydroxy, nitro or amino and, where appropriate, the optional substituent on nitrogen, (R$^8$), is —CH$_2$CO$_2$H.

When $R^2$ is an optionally substituted phenyl group, this is conveniently phenyl or phenyl substituted by one or two groups, which may be the same or different and selected from chlorine, fluorine, amino, hydroxy or carboxyl.

When $R^2$ represents the group NHR$^{11}$, $R^{11}$ is conveniently phenyl (optionally substituted by fluoro, hydroxy, amino, dimethylamino, trifluoromethylsulphonylamino, $C_{1-4}$ alkoxycarbonyl, carboxy, 1H-tetrazol-5-yl, acetylamino or OR$^{12}$ wherein R$^{12}$ represents hydrogen, methyl, benzyl, CH$_2$CO$_2$H, CH$_2$CONH$_2$, CH$_2$CONHCH$_3$, CH$_2$CON(CH$_3$)$_2$

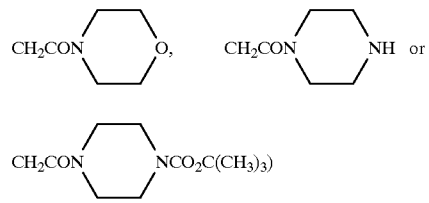

or a 7-indazolyl group wherein the N-1 substituent, (R$^{10}$), is hydrogen.

When R$^{11}$ is a mono substituted phenyl group, the substituted is conveniently in the meta- position.

Examples of particularly suitable $R^2$ groups includes indole, benzofuran, thiophene, benzothiophene, indoline, quinoline, 4-oxobenzopyran, an optionally substituted phenyl group or the group NHR$^{11}$. Conveniently, $R^2$ is selected from the group indole, indoline or benzofuran, an optionally substituted phenyl group or the group NHR$^{11}$. More particularly, $R^2$ represents an indole, an optionally substituted phenyl or NHR$^{11}$.

When $R_3$ represents $C_{1-6}$ alkyl, examples of suitable groups include methyl, ethyl, propyl, isopropyl, butyl, t-butyl or isoamyl.

When $R_3$ represents $C_{3-6}$ cycloalkyl, examples of suitable groups include cyclopropyl, cyclopentyl or cyclohexyl.

When $R_3$ represents phenyl, mono or disubstituted by independently with halogen, examples of suitable groups include those wherein the halogen substituent is fluorine e.g., 2-fluorophenyl or 4 fluorophenyl.

Examples of particularly suitable $R^3$ groups include hydrogen, methyl, cyclohexyl, 2-fluorophenyl or phenyl, and more particularly, phenyl.

A particularly useful group of compounds for use according to the invention include those wherein $R^1$ represents the group of Formula (II) wherein $R^6$ is methyl, n is 1 and $R^7$ is hydrogen, fluorine, hydroxy or methoxy, or more particularly NR$^4$R$^5$ wherein $R^4$ is propyl or isopropyl and $R^5$ is phenyl optionally substituted in the para position by a group selected from hydroxy, methoxy, fluoro, dimethylamino or monopholino; $R^2$ represents phenyl (optionally substituted independently by one or two groups selected from chlorine, fluorine, hydroxy, amine or carboxy), $NHR^{11}$ wherein $R^{11}$ represents phenyl (optionally substituted by amino, dimethylamino, trifluoromethyl- sulphonylamino, carboxy, 1H,-tetrazol-5-yl, acetylamino or $OR^{12}$ wherein $R^{12}$ represents hydrogen, methyl, benzyl, $CH_2CO_2H$, $CH_2CONH_2$, $CH_2CONHCH_3$, $CH_2CON(CH_3)_2$,

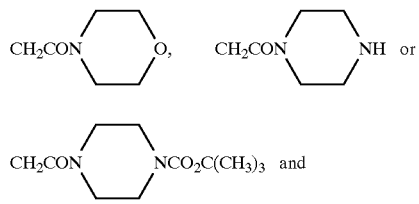

wherein the substituent is preferably in the meta- position) or an indole wherein the nitrogen atom is optionally subtituted by the group —$CH_2CO_2H$ and the benzo ring is optionally substituted by chlorine, methyl, methoxy, nitro, hydroxy or amino; $R^3$ represents hydrogen, methyl, cyclohexyl, 2- fluorophenyl or phenyl or, more particularly, 2 fluorophenyl or phenyl; and X represents fluorine and z is 1 or, more particularly, X is hydrogen;

A particularly interesting class of compounds for use in the present invention are those wherein $R^2$ is an indole group. A preferred group of compounds within this class are those wherein the indole group is substituted on the nitrogen atom by the group —$CH_2CO_2H$ or, more preferably, the nitrogen atom is unsubstituted, and benzo ring of the indole group is optionally substituted by a group selected from chlorine, methyl, methoxy, nitro, hydroxy or amino.

A particularly preferred compound for use in the invention which is hereinafter referred to as compound 'A' is:
1H-Indole-2-carboxylic acid {1-[Isopropyl-(4-methoxyphenyl)carbamoyl-methyl]-2,4-dioxo-5-phenyl-2,3,4,5-tetrahydro-1H-benzo[b][1,4]diazepin-3-yl}-amide and enantiomers thereof.

As provided herein, the term alkyl is generally intended to mean both straight chain and branched chain aliphatic isomers of the corresponding alkyl. For example, $C_{1-6}$alkyl is intended to include methyl, ethyl, n-propyl, isopropyl, n-butyl, isobutyl, tertbutyl, n-pentyl, etc.

The term cycloalkyl, as provided herein, is intended to mean all alicyclic isomers of the corresponding alkyl. For example, the term $C_{3-6}$ alkyl, as provided herein, is intended to include such groups as cyclopropyl, cyclopentyl and cyclohexyl.

The term halogen is intended to mean F, Cl, Br or I.

The term tetrazole as a group or part of a group refers to the (1 H)-tetrazol-5-yl grouping and tautomers thereof.

Those skilled in the art will recognize that stereocenters exist in compounds of Formula (I). Accordingly, the present invention includes all possible stereoisomers and geometric isomers of Formula (I) and includes not only racemic compounds but also the optically active isomers as well. When a compound of Formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Additionally, in situations where tautomers of the compounds of Formula (I) are possible, the present invention is intended to include all tautomeric forms of the compounds.

Compounds of general Formula (I) may be prepared by the general methods outlined hereinafter. In the following description, the groups X and $R^{1-12}$ are as defined for the compounds of Formula (I) unless stated otherwise.

Compounds of general formula (I) and salts thereof may be prepared by the general methods outlined hereinafter. In the following description, the groups $R_1$—$R^{12}$ and X are as defined for the compounds of formula (I) unless otherwise stated.

According to a first general process A, compounds of formula (I) may be prepared by the reaction of an amine of formula (III) wherein $R^1$, $R^2$, $R^3$, X and z have the meanings defined in formula (I)

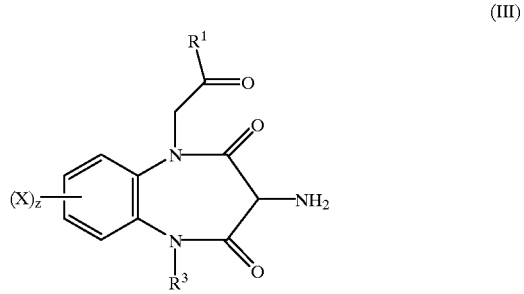

with a compound $R^{11}Y$ (IV) wherein Y is the group —NCO, HNCOCl or $NHCOR_a$ where $R_a$ is nitro substituted phenoxy group or a 1-imidazole group.

The reaction conveniently takes place in the presence of a suitable solvent such as a halohydrocarbon (e.g. dichloromethane), an ether (e.g. tetrahydrofuran) or nitrile (e.g. acetronitrile) or a mixture thereof at a temperature in the range of 0°–80° C.

Compounds of formula (IV) wherein Y is —NCO) may be purchased or prepared by the reaction of amines $H_2N$—$R^{11}$ with phosgene or triphosgene in a suitable solvent such as methylene chloride. Compounds of formula (IV) wherein Y is NHCOCl are also prepared by the reaction of amines $H_2NR^{11}$ with phosgene or triphosgene in a suitable solvent such as methylene chloride. Compounds of formula (IV) wherein Y is $NHCOR_a$ and $R_a$ is a 1-imidazole group are prepared by treatment of amines $H_2N$—$R^{11}$ with carbonyl diimidazole in a suitable solvent (dichloromethane, ether, tetrahydrofuran) at a temperature ranging from 0–80° C. (conveniently at room temperature). Compounds of formula (IV) wherein Y is $HNCOR_a$ and $R_a$ is a nitro substitued phenxoy group are prepared by the reaction of amines $H_2N$—$R^{11}$ with the appropriate chloroformate $R_aCOCl$ in the presence of a base (pyridine, triethylamine) in a suitable solvent (dichloromethane) and at a temperature of 0–50° C.

According to a further general process B, compounds of formula (I) may be prepared by reaction of an intermediate of formula (V).

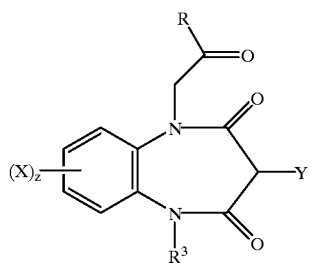

wherein Y is the group —NCO, —NHCOCl or NHCOR$_a$ wherein R$_a$ is a nitro substituted phenoxy group or a 1-imidazole group with an amine (VI)

and optionally in the the presence of a base such as a tertiary amine (e.g. triethylamine).

The reaction conveniently takes place in a suitable solvent such as a halogenated hydrocarbon (e.g. dichloromethane) or an ether (e.g. tetrahydrofuran) or an amide (e.g. N,N-dimethyl formamide) optionally at a temperature ranging from room temperature to the reflux temperature of the solvent.

Conveniently the compounds of formula (V) are prepared in situ from the amine (III).

In a particular aspect of the process (B) when Y is the group NHCOR$_a$ and R$_a$ is a 1-imidazole group, the imidazolide (V) may be formed in situ in which case the amine of formula (VI) will be mixed with the compound of formula (III)

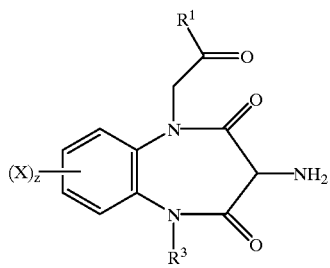

in the presence of carbonyldiimidazole under the aforementioned conditions.

For process B when Y is the group NHCOR$_a$ and R$_a$ is a nitro substituted phenoxy group the reaction with the primary amine (VI) is preferably carried out in the presence of a base such as a tertiary amine e.g. triethylamine.

For process B when Y is the isocyanate group —N=C=O the reaction with the primary amine (VI) is preferably carried out in an aprotic solvent such as a halohydrocarbon e.g. methylene chloride. Conveniently the isocyanate is generated in situ prior to the addition of the primary amine (VI).

The compounds of formula (V) wherein R$_a$ is an optionally substituted phenoxy group may be prepared from the primary amine (III) by reaction with the corresponding nitro substituted phenyl chloroformate in the presence of a base such as pyridine. The reaction may be carried out in a solvent such as a halohydrocabon e.g. dichloromethane and at a temperature from 0–50°.

Compounds of formula (V) wherein R$_a$ is a 1-imidazole group may be prepared by reacting a compound of formula (III) with carbonyldiimidazole in the presence of a suitable solvent such as a halogenated hydrocarbon (e.g. dichloromethane) or an ether (e.g. tetrahydrofuran) at a temperature ranging from 0° to 80° (conveniently at room temperature).

Compounds of formula (V) wherein Y is the isocyanate grouping —N=C=O or carbamoyl chloride —NHCOCl may be prepared from the primary amine (III) by reaction with phosgene (COCl$_2$) or triphosgene in a suitable solvent such as methylene chloride.

According to a further general process C compounds of formula (I) may also be prepared by a reaction of the compound of formula (VII)

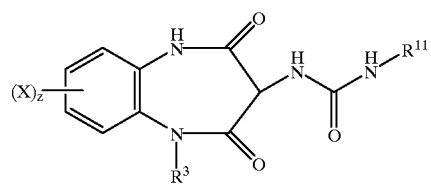

with an acetylbromide or chloride having the formula (VIII)

wherein hal=Cl or Br.

The reaction is conveniently carried out by treating the compound of formula (VII) with a strong base such as sodium hydride in a polar aprotic solvent such as N,N-dimethylformamide followed by reaction with the acetyl halide (VIII).

The acetyl halide (VIII) is prepared by the reaction of the amine R$^1$-H with corresponding haloacetyl bromide in dichloromethane at 0° C., with a suitable base, such as triethylamine.

The amines R$^1$—H wherein R$^1$ is the group —NR$^4$R$^5$, may be prepared by the reductive alkylation of the amine H$_2$N—R$^5$ with an appropriate aldehyde or ketone.

According to general process D, compounds of general Formula (I) may also be prepared by the reaction of the intermediate of Formula (III) with acids of Formula (IX), as set forth below.

Thus reaction of the intermediates of formula (III) with the acid of formula (IX) may be carried out in the presence of a suitable dehydrating agent such as dicyclohexylcarbodiimide (DCC), 1-(3-dimethylaminopropyl)-3-ethylcarbodiimide hydrochloride (EDC) or bis(2-oxo-3-oxazolidinyl)phosphinic chloride (BOP).

Alternatively, compounds of general Formula (I) may be obtained by reaction of the intermediates of Formula (III) with an activated derivative of the acid (IX) such as an acid chloride or anhydride thereof, including mixed anhydrides.

Preferred solvents for general process D include N,N-dimethylformamide or dichloromethane. Preferred temperatures are between 0–60° C. Preferred bases for this reaction include triethylamine or N,N-dimethylaminopyride (DAMP).

According to a further general process (E) compounds of the invention may be converted into other compounds of the invention. Thus for example compounds of formula (I) wherein $R^8$ is the group $(CH_2)_b CO_2 H$ may be preapred by reaction of a compound of formula (I) wherein $R^8$ is hydrogen with compound $Br(CH_2)_b COOR^*$ wherein $R^*$ is $C_{1-4}$alkyl in the presence of a strong base such as sodium hydride followed by removal of the carboxy protecting group by conventional procedures e.g. acidic or basic hydrolysis Compounds of formula (III) may be prepared by reduction of compounds of formula (X)

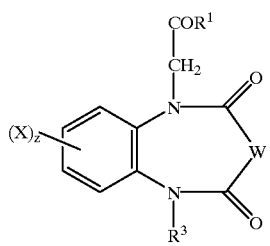

(X)

wherein W is CH—$N_3$ or C=N—NHPh.

Compounds of formula (X) wherein W is CH—$N_3$ may be reduced to a compound of formula (III) by hydrogenation in the presence of a suitable catalyst such as 5–10% palladium on a support such as carbon or calcium carbonate, or platinum (IV) oxide. The reaction conveniently takes place in the presence of a solvent such as an alkanol (e.g. ethanol) an ester (e.g. ethyl acetate) or acetic acid.

Compounds of formula (X) wherein W is C=N—NHPh may be reduced to a compound of formula (III) by reaction with zinc and acetic acid. This reaction may be carried out a temperature with the range 0–50°.

Compounds of formula (X) wherein W is $CHN_3$ may be prepared from a compound of formula (X) wherein W is $CH_2$ by treatment with a strong base such as sodium hydride or potassium tert-butoxide followed by tri-isopropyl benzenesulphonyl azide or di-tertbutoxyazidodicarboxylate. The reaction conveniently takes place in a solvent such as an ether (e.g. tetrahydrofuran) at a temperature in the range of −78° to 20°.

Compounds of formula (X) in which W is C=NNHPh or $CH_2$ may be prepared by reaction of the ortho-phenylenediamine (XI) with the diacid chloride (XII) wherein Q is $CH_2$ or C=NNHPh, in a suitable solvent such as an ether e.g. tetrahydrofuran

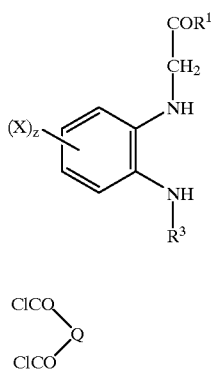

The compound of formula (XII) wherein Q is C=NNHPh may be prepared by reaction of ketomalonic acid with phenyl hydrazone followed by reaction with phosphorus pentachloride.

Compounds of formula (XI) are either known compounds or may be prepared by analogous methods. Thus for example a compound of formula (XI) may be prepared by alkylation of the amine (XIII).

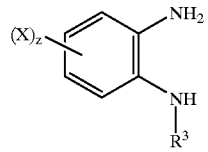

Thus the amine (XIII) may be reacted with the compound $R_1 COCH_2$hal wherein hal is chlorine or bromine, optionally in the presence of sodium iodide in a solvent such as N,N-dimethylformamide.

An alternative preparation of the intermediate of Formla (III) as set forth below, involves treatment of the intermediate of Formula (XIV) with sodium hydride followed by addition of an acetyl halide (VIII) in a suitable solvent, such as N,N-dimethyl formamide, at 0° C. to provide the protected intermediate of Formual (XV)

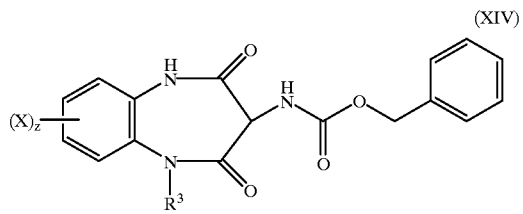

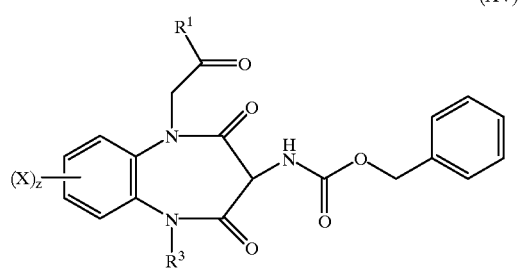

Intermediate (XV) is converted to the required amine (III) by catalytic hydrogenation (40–60 psi) using a suitable catalyst, such as 5–10% pd/C, in a suitable solvent, such as methanol, ethanol, ethyl acetate, chloroform or acetic acid, at room temperature. Alternatively, intermediate (XVI) may be converted to amine (III) by treatment with HBr in methylene chloride.

Intermediate (XIV) is obtained from the intermediate of Formula (XVI) by reaction with benzyloxychloroformate in dichloromethane, using triethylamine as base. This reaction is run conveniently at room temperature.

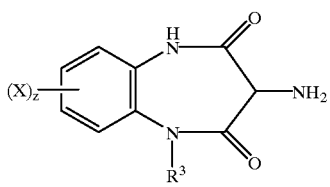

Intermediate (XVI) is prepared from phenylene diamine (XIII) by the following process.

Reaction of the diamine (XIII) with p-methyoxylbenzoylochloride followed by reduction of the amide thus formed with lithium aluminum hydride yields the N-protected diamine (XVII)

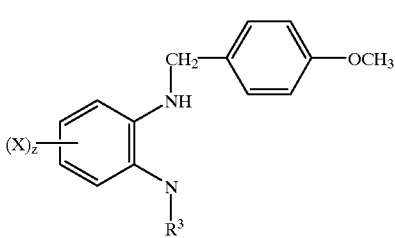

Reaction of compound (XVII) with the diacid chloride (XII; Q=C=NNHPh) followed by reduction with zinc and acetic acid yields the amine (XVIII)

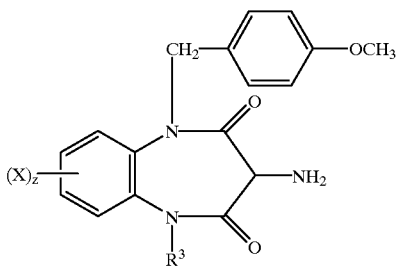

The compound of formula (XVIII) may be converted into the required compound (XVI) by rection with $Ce(NO_2)_6NH_4$ (ceric ammonium nitrate).

Compounds of formula (I) contain at least one asymmetric carbon atom, namely the carbon atom of the diazepine ring to which the substituted urea grouping is attached. Specific enantiomers of the compounds of formula (I) may be obtained by resolution of the racemic compound using conventional procedures such as chiral HPLC. Alternatively the required enantiomer may be prepared from the corresponding enantiomeric amine of formula (III) using any of the processes described above for preparing compounds of formula (I) from the amine (III). The enantiomers of the amine (III) may be prepared from the racemic amine (II) using conventional procedures such as salt formation with a suitably optically active acid or by preparative chiral HPLC.

EXAMPLES

The following examples are set forth to illustrate the synthesis of some particular compounds for use in the invention. Accordingly, the following Example section is in no way intended to limit the scope of the invention contemplated herein.

General Procedures

Unless otherwise noted, all starting materials were obtained from commercial suppliers and used without further purification. The following solvents and reagents have been described by acronyms: tetrahydrofuran (THF), dimethylsulfoxide (DMSO), dichloromethane (DCM), trifluoroacetic acid (TFA), dimethylformamide (DMF), 1,1-carbonyldiimidazole (CDl), isobutylchloroformate (iBuCF) N-hydroxysuccinimide (HOSu), N-hydroxybenztriazole (HOBT), 1 -(3-dimethylaminopropyl)-3-ethylcarbodiimide hydrochloride (EDC), bis(2-oxo-3-oxazolidinyl) phosphinic chloride (BOP), tert-butyloxycarbonyl (BOC), benzyloxycarbonyl (Cbz).

The $^1$HNMR spectra were recorded on either a Varian VXR-300 or a Varian Unity-300 instrument. Chemical shifts are expressed in parts per million (ppm, d units). Coupling constants are in units of hertz (Hz). Splitting patterns are designated as s, singlet; d, doublet; t, triplet; q, quartet; m, multiplet; b, broad.

Low-resolution mass spectra (MS) were recorded on a JOEL JMS-AX505HA, JOEL SX-102 or a SCIEX-APliii spectrometers. All mass spectra were taken in the positive ion mode under electrospray ionization (ESl), chemical ionization (Cl), electron impact (El) or by fast atom bombardment (FAB) methods. Infrared (IR) spectra were obtained on a Nicolet 510 FT-IR spectrometer using a 1-mm NaCl cell. Rotations were recorded on a Perkin-Elmer 241 polarimeter. All reactions were monitored by thin-layer chromatography on 0.25 mm E. Merck silica gel plates (60F-254), visualized with UV light, 7% ethanolic phosphomolybdic acid or p-anisldehyde solution. Flash column chromatography was performed on silica gel (230–400 mesh, Merck).

Products were purified by preparative reversed phase high pressure liquid chromatography (RP-HPLC) using a Waters Model 3000 Delta Prep equipped with a Delta-pak radial compression cartridge ($C_{18}$, 300 A, 15 m, 47 mm×300 mm). Linear gradients were used in all cases and the flow rate was 100 ml/minute ($t_0$5.0 min.). All solvents contained 0.1% trifluoroacetic acid (TFA). Analytical purity was assessed by RP-HPLC using a Waters 600E system equipped with a Waters 990 diode array spectrometer (t range 200–400 nM). The stationary phase was a Vydac $C_{18}$ column (5 m, 4.6 mm×250 mm). The flow rate was 1.0 to 1.5 ml/min. ($t_0$=2.8 or 3.0 min.) and the solvent systems were as described above. Data reported as tr, retention time in minutes (% acetonitrile over time).

Using the general processes A–E outlined above, the following compounds of formula (I) have been made.

Example 1

2-[2,4-Dioxo-5-phenyl-3-(3-phenyl-ureido)-2,3,4,5-tetrahydro-benzo[b] [1,4] diazepin-1-yl]-N-isopropyl-N-phenyl-acetamide To a solution of 1-(2,4-dioxo-1-phenyl-2,3,4,5-tetrahydro-1H-benzo [b] [1,4]-diazepin-3-yl)-3-phenyl urea (0.100 g.) in N,N-dimethylformamide (2 ml) cooled to 3° C., was added sodium hydride (0.0104 g; 60% suspension in mineral oil) with stirring. The mixture was stirred 20 minutes, then 2-bromo-N-isopropyl-N-phenyl acetamide (0.0656 g) was added in one portion. The resultant mixture was stirred at ambient temperature overnight. The crude reaction mixture was purified by preparative RP-HPLC with a gradient elution of 60–72% acetonitrile in water with 0.1% trifluoroacetic acid buffer over a 30 minute period at a rate of 100 ml/min. Fractions containing the desired material were combined, frozen and lyophilized to provide the title compound (0.0653 g) as a white powder. $^1$H NMR (300 MHz, DMSO-$d_6$): d 0.95 (d, J=7.3 Hz, 3H), 0.98 (d, J=7.3 Hz, 3H), 4.19 (d, J=16.6 Hz, 1H), 4.48 (d, J=16.9 Hz, 1H), 4.79 (m, 1H), 5.04.(d, J=7.8 Hz, 1H), 6.87–6.92(m, 1H), 6.95(d, J=7.6 Hz, 1H), 7.18–7.57 (m, 17H), 9.14 (s, 1H); MS (FAB): m/z=562 (MH$^+$);TLC (CH$_2$Cl$_2$/CH$_3$OH, 19:1): R$_f$=0.19; RP-HPLC (Vydac C-18, 25 cm×4.6 mm; 60–72% CH$_3$CN in H$_2$O with 0.1% TFA buffer; 30 minutes; 1 ml/min): t$_r$=17.5 min (t$_0$=2.5 min); m.p.: 230–235° C.

Enantiomers of the title compound (0.014 g) were separated on a Pirkle covalent (L)-Phenylglycine column, 25 cm×10.0 mm, with an isocratic eluant of methanol/water (80:20) at a rate of 5 ml/min. Fractions from the four injections corresponding to the first eluted enantiopode were combined and evaporated under reduced pressure to give enantiomer 1 as a white powder. Likewise, fractions corresponding to the second eluted enantiopode were combined and evaporated under reduced pressure to give entantiomer 2 as a white powder.

Enantiomer 1: Chiral HPLC (Pirkle covalent (L)-Phenylglycine, 25 cm×4.6 mm; CH$_3$OH/H$_2$O (78:22) isocratic; 1.5 ml/min): tr=14.5 min (t$_0$=2 min); MS (FAB): m/z=562.1 (MH$^+$)

Enantiomer 2: Chiral HPLC (Pirkle covalent (L)-Phenylglycine, 25 cm×4.6 mm; CH$_3$OH/H$_2$O (78:22) isocratic; 1.5 ml/min): t$_r$=18 min (t$_0$=2 min); MS (FAB): m/z=562.0 (MH$^+$)

Example 2

1H-Indole-2-carboxylic acid [1 -(Isopropyl-phenyl-carbamoylmethyl)-2,4-dioxo-5-phenyl-2,3,4,5-tetrahydro-1H-benzo[b][1,4]diazepin-3-yl]-amide To a vigorously stirred solution of 2-(3-Amino-2,4-dioxo-5-phenyl-2,3,4,5-tetrahydro-benzo [b] [1, 4] diazepine-1-yl)-N-isopropyl-N-phenyl acetamide (0.116 g) in N,N-dimethylformamide (5 ml) at ambient temperature was added indole-2-carboxylic acid (0.0423 g, 0.262 mmol), N-hydroxybenzotriazole (0.0354 g), and 1-(3-dimethylaminopropyl)-3-ethylcarbodiimide hydrochloride (0.0503 g) successively. Triethylamine (8 drops) was added dropwise to maintain the basicity (pH=9) of the solution was reached. The resultant mixture was stirred at ambient temperature for five hours. The solvent was evaporated in vacuo to give a yellow oil which was purified by flash chromatography on silica gel (9 g) with an eluant of a mixture of ethyl acetate and hexane (2:3, 200 ml). Fractions containing the desired product were combined and evaporated in vacuo to give the title compound (0.141 g) as a white foam. $^1$H NMR (300 MHz, CDCl$_3$): d 1.06 (d, J=7.3 Hz, 3H), 1.09 (d, J=7.3 Hz, 3H), 4.22 (d, J=16.6 Hz, 1H), 4.40(d, J=16.4 Hz, 1H), 5.02(m, 1H), 5.50(d, J=7.1 Hz, 1H), 7.02(d, J=8.1 Hz, 1H), 7.10–7.47 (m, 16H), 7.57 (d, J=6.8 Hz, 1H), 7.67 (d, J=7.8 Hz, 1H), 9.29 (br s, 1H); MS (FAB): m/z=586.0 (MH$^+$); TLC (EtOAc/Hexane (2:3)): R$_f$=0.16; RP-HPLC (Vydac C-18, 25 cm×4.6 mm; 51–60% CH$_3$CN in H$_2$O with 0.1% TFA buffer; 30 minutes; 1 ml/min): t$_r$=19.5 min (t$_0$=3 min)

Example 3

1H-Indole-2-carboxylic acid {1-[Isopropyl-(4-methoxyphenyl)carbamoyl-methyl]-2,4-dioxo-5-phenyl-2,3,4,5-tetrahydro-1H-benzo[b][1,4]diazepin-3-yl}-amide To a solution of 2-(3-Amino-2,4-dioxo-5-phenyl-2, 3, 4, 5-tetrahydro-benzo [b] [1,4] diazepine-1-yl)-N-isopropyl-N-(4-methoxy-phenyl)-acetamide (500 mg) in N,N-dimethylformamide (15 mL) were added indole-2-carboxylic acid (174 mg), N-hydroxybenzotriazole (143 mg), and 1-(3-dimethylaminopropyl)-3-ethylcarbodiimide hydrochloride (0.203 g) successively with stirring at ambient temperature. The resultant mixture was stirred at ambient temperature for 18 hours. The solvent was evaporated under reduced pressure to give a yellow oil which was taken into ethyl acetate(75 mL), washed with water (2×30 mL), dried over sodium sulfate, filtered and concentrated under reduced pressure to a give a tan foam. The crude product was purified via preparative HPLC chromatography on a Delta-Pak C-18 column eluted with a linear gradient from 50% to 60% acetonitrile in water with 0.1% trifluoroacetic acid buffer over a 30 minute period at a rate of 100 mL/min. Appropriate fractions were combined, frozen and lyophilized to give the TFA salt of the title compound (0.550 g) as a white powder.

$^1$H NMR (300 MHz, CDCl$_3$): d 1.06(m, 6H), 3.85(s, 3H), 4.27(d, J=16.6 Hz, 1H), 4.34(d, J=16.6 Hz, 1H), 4.99(m, 1H), 5.51(d, J=7.4 Hz, 1H), 6.96–7.42(m, 17H), 7.66(m, 2H), 9.54(br s, 1H)

TLC (dichloromethane/methanol(9:1)): R$_f$=0.64

MS (FAB): m/z=616.2 (MH$^+$) (calcd. for C$_{36}$H$_{33}$N$_5$O$_5$= 615.2484)

Example 4

2-[1-(Isopropyl-phenyl-carbamoylmethyl)-2,4-dioxo-5-phenyl-2,3,4,5-tetrahydro-1H-benzo[b][1,4]diazepin-3-ylcarbamoyl]-indol-1-yl-acetic acid.

To a vigorously stirred solution of 1H-indole-2-carboxylic acid [1-(Isopropyl-phenyl-carbamoylmethyl)-2,4-dioxo-5-phenyl-2,3,4,5-tetrahydro-1H-benzo[b][1,4]diazepin-3-yl]-amide (0.101 g) in N,N-dimethylformamide (3 ml) cooled to 3° C. was added sodium hydride (0.0083 g) (60% suspension in mineral oil). After 20 minutes, t-butylbromoacetate (0.0336 g) was added. The resultant mixture was stirred with cooling in an ice bath for 90 minutes followed by slow warming to ambient temperature and stirring overnight. The solvent was evaporated under reduced pressure to give a brown oil which was dissolved in dichloromethane (30 ml) and washed successively with saturated aqueous sodium bicarbonate (20 ml) and brine (20 ml). The resultant solution was dried over sodium sulfate, filtered and evaporated under reduced pressure to give a yellow oil (0.142 g) which was purified by flash chromatography on silica gel (9 g) with an eluant of a mixture of ethyl acetate and hexane (1:2, 200 ml). Fractions containing the desired product were combined and evaporated to give 2-[1-(Isopropyl-phenyl-carbamoylmethyl)-2,4-dioxo-5-phenyl-2,3,4,5-tetrahydro-1H-benzo[b][1,4]diazepin-3-ylcarbamoyl]-indol-1-yl}-acetic acid tert-butyl ester (0.092 g) as a white foam. $^1$H NMR (300 MHz, CDCl$_3$): d 1.07 (d, J=4.9 Hz, 3H), 1.09 (d, J=4.6 Hz,3H), 1.37 (s,9H),4.17 (d,J=16.6 Hz, 1H),4.44(d,J=16.9 Hz, 1H), 5.01 (m, 1H), 5.18 (d, J=17.1 Hz, 1 H), 5.24 (d, J=18 Hz, 1H), 5.47 (d, J=7.6 Hz, 1H), 7.01 (dd, J=1.2, 8.3 Hz, 1H), 7.13–7.51 (m, 17H), 7.57 (d, J=7.3 Hz, 1H), 7.67 (d, J=7.8 Hz, 1H); MS (FAB): m/z=700.2 (MH$^+$); TLC (EtOAc/Hexane, 2:3): R$_f$=0.35; RP-HPLC (Vydac C-18, 25 cm×4.6 mm; 60–70% CH$_3$CN in H$_2$O with 0.1% TFA buffer; 30 minutes; 1 ml/min): t$_r$=17.5 min (t$_0$=3 min)

To a solution of {2-[1-(Isopropyl-phenyl-carbamoylmethyl)-2,4-dioxo-5-phenyl-2,3,4,5-tetrahydro-1H-benzo[b][1,4]diazepin-3-ylcarbamoyl]-indol-1-yl}- acetic acid tert-butyl ester (0.072 g) in dichloromethane (4 ml) at ambient temperature was added trifluoroacetic acid (1.5 ml) gradually with stirring. After the reaction was stirred 30 minutes, the dichloromethane and trifluoroacetic acid were evaporated under reduced pressure to afford a clear glass. The glass was purified by preparative RP-HPLC on a C-18 column with a gradient elution of 45–55% acetonitrile in water with 0.1% trifluoroacetic acid buffer over a 30 minute period at a rate of 100 ml/min. Fractions containing the desired material were combined, frozen and lyophilized to afford the title compound (0.050 g) as a white powder. $^1$H NMR (300 MHz, CDCl$_3$): d 1.07 (d, J=4.4 Hz, 3H), 1.10 (d, J=4.4 Hz, 3H), 4.23 (d, J=16.6 Hz, 1H), 4.40 (d, J=16.6 Hz, 1H), 5.01 (m, 1H), 5.06 (s, 2H), 5.44 (d, J=7.1 Hz, 1H), 7.03 (dd, J=1.2, 8.1 Hz, 1H), 7.17–7.52 (m, 17H), 7.67 (d,J=8.1 Hz, 1H), 7.74 (d,J=7.1 Hz, 1H); MS (ES): m/z=644.2 (MH$^+$);TLC (CH$_2$Cl$_2$/CH$_3$OH(19:1)): R$_f$=0.15; RP-HPLC (Vydac C-18, 25 cm×4.6 mm; 45–55% CH$_3$CN in H$_2$O with 0.1% TFA buffer; 30 minutes; 1 ml/min): t$_r$=22 min (t$_o$=3 min).

Example 5

2-(2,4-dioxo-5-phenyl-3-{3-[3-(1H-tetrazol-5-yl)-phenyl]-ureido}2,3,4,5-tetrahydro-benzo[b][1,4] diazepin-1-yl) N-isopropyl-N-phenylacetamide To a vigorously stirring solution of 2-(3-amino-2,4-dioxo-5-phenyl-2,3,4,5-tetrahydrobenzo[b][1,4]diazepin-1-yl)-N-isopropyl-N-phenyl-acetamide (0.070 g) in tetrahydrofuran (3 ml) at ambient temperature was added 1,1-carbonyldiimidazole (0.025 g) in one portion. The resulting mixture was stirred for 90 minutes at ambient temperature. 3-(2H-tetrazol-5-yl)-phenylamine hydrochloride (31.3 mg), was added in one portion and the reaction mixture was heated to reflux overnight. The reaction mixture was filtered and the filtrate concentrated to a yellow oil. The oil was purified by preparative RP-HPLC on a C-18 column with a gradient elution of 43–53% acetonitrile in water with 0.1% trifluoroacetic acid buffer over a 30 minute period at a rate of 100 ml/min. Fractions containing the desired material were combined, frozen and lyophilized to provide the title compound as a white powder (50 mg).

$^1$H NMR (300 MHz, DMSO-d$_6$): d 0.96(d, J=7.3 Hz, 3H), 0.98(d, J=7.3 Hz, 3H), 4.20(d, J=16.8 Hz, 1H), 4.49(d, J=17.1 Hz, 1H), 4.79(m, 1H), 5.06(d, J=7.3 Hz, 1H), 6.98(m, 2H), 7.24–7.55(m, 17H), 8.17(s, 1H), 9.44(s, 1H)

MS (FAB): m/z=630.2 (MH$^+$) (calcd. for C$_{34}$H$_{31}$N$_9$O$_4$= 629.2502)

TLC (CH$_2$Cl$_2$/CH$_3$OH(9:1)): R$_f$=0.24

RP-HPLC (Vydac C-18, 25 cm×4.6 mm; 43–53% CH$_3$CN in H$_2$O with 0.1% TFA buffer; 30 minutes; 1 ml/min): t$_r$=15 min (t$_0$=3 min)

Example 6

3-{3-[1-(Isopropyl-phenyl-carbamoylmethyl)-2,4-dioxo-5-phenyl-2,3,4,5-tetrahydro-1H-benzo[b][1,4] diazepine-3-yl]-ureido}benzoic acid ethyl ester A solution of 3-ethoxycarbonyl phenylisocyanate (124 mg) in dichloromethane (3 ml) was ,added to a solution of 2-(3-amino-2,4-dioxo-5-phenyl-2,3,4,5-tetrahydrobenzo[b] [1,4]diazepin-1-yl-N-isopropyl-N-phenylacetamide (288 mg), in dichloromethane (3 ml). The reaction was allowed to stir at room temperature for 30 minutes. The dichloromethane was evaporated in vacuo and the residue was suspended in acetonitrile and heated at reflux for 1 hour with stirring. Compound 40 precipitated upon cooling to 0° C. The filtrate was washed with cold acetonitrile to give the title compound as a white solid (312 mg, 76%). $^1$H-NMR (300 MHz, d$_6$-DMSO): d 9.4 (s, 1H), 8.05 (s, 1H), 7.6–6.9 (m, 18H), 5.05 (d, 9 Hz, 1H), 4.8 (m, 1H), 4.48 (d, 16 Hz, 1H), 4.3 (dd, 6.8 Hz, 2H), 4.18 (d, 15.8 Hz, 1 H), 1.27 (t, 7.2 Hz, 3H), 0.96 (m, 6H); MS (FAB)=634 (MH$^+$).

Example 7

3-{3-[1-(Isopropyl-phenyl-carbamoylmethyl)-2,4-dioxo-5-phenyl-2,3,4,5-tetrahydro-1H-benzo[b][1,4] diazepine-3-yl]-ureido} benzoic acid A solution of 3-{3-[1 -(Isopropyl-phenyl-carbamoylmethyl)-2,4-dioxo-5-phenyl-2,3,4,5-tetrahydro-1H-benzo[b][1,4]diazepine-3-yl]-ureido} benzoic acid ethyl (312 mg, 0.493 mol) in methanol (23 ml) and tetrahydrofuran (10 ml) was heated to reflux. Aqueous 5% potassium carbonate (6.5 ml) is added and the reflux was maintained for 2.5 hours. The reaction mixture was concentrated in vacuo and the residue was neutralized and triturated with 1N HCl and water to give the crude product. The crude product was dissolved in ethyl acetate (20 ml), heated to reflux for 3 hours then cooled. The resulting precipitate was separated by filtration and dried under vacuum to provide the title compound as a white solid (225 mg, 75%). $^1$H-NMR (300 MHz, d$_6$-DMSO): d 9.4 (s, 1H), 8.05 (s, 1H), 7.6–6.9 (m, 18H), 5.05 (d, 9 Hz, 1H), 4.8 (m, 1H), 4.48 (d, 16 Hz, 1H), 4.18 (d, 15.8 Hz, 1H), 0.96 (m, 6H); MS (FAB)=606 (MH$^+$).

The aforementioned Examples are set forth so as to better illustrate synthesis approaches for preparing the compounds of the present invention. Additionally, particular intermediates useful in the general processes set forth herein can be prepared as set forth below.

Intermediate 1

2-(phenylhydrazono)-malonic acid

To a vigorously stirred solution of ketomalonic acid monohydrate (29.33 g) in ethanol (140 ml) and water (300 ml) at ambient temperature was added phenylhydrazine (23.3 g) dropwise over a 40 minute period. The resultant slurry was stirred overnight at ambient temperature. The solid was separated by filtration, washed sucessively with cold water (100 ml) and ethanol (25 ml) and air dried. Subsequent drying was performed at 75° C. overnight in a vacuum oven to give the title compound as a yellow solid (42.38 g). $^1$H (300 MHz, DMSO-d$_6$): d 7.12(t, 1H), 7.35–7.48(m, 4H); m.p.: 155–157° C. (dec).

Intermediate 2

2-(phenylhydrazono)-propanedioyl dichloride

To a stirred slurry of Intermediate 1 (14.73 g), in chloroform (90 mL) at 5° C. was added phosphorous pentachloride (36.84 g) portionwise over a 20 minute period. After complete addition, the solution was warmed to room temperature and stirred one hour followed by heating to reflux for three hours. The solution was cooled in an ice bath and the resultant precipitate was separated by filtration, washed with cold hexane (50 ml), and dried under vacuum overnight to give the title compound (13.4 g) as a bright yellow solid. 1H (300 MHz, DMSO-d$_6$): d 7.12(t, 1H), 7.20–7.56(m, 4H); m.p.: 135–138° C. (dec).

Intermediate 3

4-methoxy-N-(2-phenylaminophenyl)benzamide

A vigorously stirring solution of N-phenyl-1,2-phenylenediamine (20.15 g) in dichloromethane (325 ml)

and triethylamine (11.07 g) was cooled in an ice/acetone bath under nitrogen. p-Anisoyl chloride (18.66 g) dissolved in dichloromethane (100 ml) was added dropwise over a 20 minute period while maintaining a temperature of <5° C. The reaction mixture was allowed to warm to ambient temperature and stirred for two hours. The organic solution was washed successively with water (200 ml), 2N aqueous HCl (80 ml), and saturated brine solution (160 ml), then dried over sodium sulfate and passed through a pad of silica (150 g). The silica was eluted with ethyl acetate (1 L) and the eluent was evaporated in vacuo to a pink solid. The solid was triturated overnight with ethyl ether (350 ml), cooled in an ice bath, filtered, and dried in vacuo to give the title compound as a light pink solid (21.67 g). $^1$H (300 MHz, CDCl$_3$): d 3.82 (s, 3H), 5.75 (br s, 1H), 6.80–6.91(m, 5H), 7.12–7.29 (m, 5H), 7.62 (d, J=8.8 Hz, 2H), 8.15 (dd, J=1.7, 7.8 Hz, 1H), 8.36 (s, 1H); TLC (EtOAc/Hex, 1:4): R$_f$=0.24; m.p.: 148–150° C.

Intermediate 4

N-(4-Methoxybenzyl)-N'-phenyl-benzene-1,2-diamine

To a stirred solution of lithium aluminum hydride (1.0 g) in THF (40 ml) cooled to 5° C. was added a solution of 4-methoxy-N-(2-phenylamino-phenyl)-benzamide (5.0 g) in THF (30 ml) over a 45 minute period. After complete addition, the reaction mixture was heated to reflux for 1.5 hrs. The solution was cooled to room temperature and excess lithium aluminum hydride was quenched with ethanol until hydrogen evolution ceased. Saturated agueous sodium hydrogen carbonate (100 ml) was added and the resultant solution extracted with ethyl acetate (3×100 ml). The combined organic extracts were dried with sodium sulfate and filtered through a pad of silica. The silica pad was washed with ethyl acetate (500 ml) and the organic fractions were combined. The filtrate was concentrated in vacuo to a brown oil which solidified on standing to give the title compound. (4.78 g). $^1$H (300 MHz, CDCl$_3$): d 3.79 (s, 3H), 4.27 (s, 2H), 4.52 (br s, 1H), 5.08 (s, 1H), 6.67–6.74 (m,4H), 6.79–6.86 (m, 3H), 7.04–7.24 (m, 6H); TLC (EtOAc/Hex (1:4)): R$_f$=0.57

Intermediate 5

1-(4-Methoxybenzyl)-5-phenyl-3-(phenylhydrazono)-1,5-dihydro-benzo [b] [1,4] diazepine-2,4-dione Solutions of Intermediate 4 (4.86 g) in THF (40 ml) and 2-(phenylhydrazono) propandioyl dichloride (5.58 g) in THF (40 ml) were added concomitantly dropwise with stirring in an ice/methanol bath over a 30 minute period. The solution was allowed to warm to room temperature and stirred overnight. A yellow precipitate was separated by filtration, washed with cold THF (40 ml), air dried and dried in vacuo overnight to give the title compound (6.23 g) as a yellow solid. $^1$H (300 MHz, CDCl$_3$): d 3.78 (s, 3H), 4.69 (d, J=14.7 Hz,1H), 5.76 (d, J=14.9 Hz, 1H), 6.80–6.87 (m, 3H), 7.02–7.12 (m, 4H), 7.19–7.40 (m, 1 1H), 11.19 (s, 1H); MS (FAB): m/z=477.0 (MH$^+$); TLC (EtOAc/Hex, 1:4): R$_f$=0.18

Intermediate 6

3-Amino-1-(4-methoxybenzyl)-5-phenyl-1,5-dihydrobenzo[b][1,4] diazepine-2,4-dione To a vigorously stirred slurry of zinc dust (6.49 g) in acetic acid (50 ml) cooled to 10° C., was added a slurry of 1-(4-Methoxybenzyl)-5-phenyl-3-(phenylhydrazono)-1,5-dihydrobenzo [b] [1,4] diazepine-2,4-dione (5.75 g,12.1 mmol) in acetic acid (30 ml) over a fifteen minute period. After complete addition, the solution was warmed to room temperature and stirred three hours. The zinc was separated by filtration and washed with ethyl acetate (75 ml). The filtrate was concentrated in vacuo and partitioned between H$_2$O (60 ml) and ethyl acetate (100 ml). The pH was adjusted to 9 with saturated aqueous sodium carbonate and the phases separated. The aqueous phase was extracted with ethyl acetate (2×75 ml), the organic layers combined, dried with magnesium sulfate, filtered and concentrated in vacuo to give a yellow oil which was dried in vacuo to give the title compound (4.79 g) NMR (300 MHz, CDCl$_3$): d 3.05 (s, 2H), 3.75 (s, 3H), 4.35 (s, 1H), 4.64 (d, J=14.7 Hz, 1H), 5.82 (d, J=14.7 Hz, 1H), 6.59–6.85 (m, 6H), 7.06–7.29 (m, 6H), 7.51 (d, J=7.4 Hz, 1H); MS (FAB): m/z=388.2 (MH$^+$); TLC (CH$_2$Cl$_2$/CH$_3$OH (9:1)): R$_f$=0.50

Intermediate 7

3-Amino-1-phenyl-1,5-dihydrobenzo[b][1,4] diazepine-2,4-dione

To a stirred solution of 3-amino-1-(4-methoxybenzyl)-5-phenyl-1,5-dihydrobenzo [b] [1,4] diazepine-2,4-dione (0.50 g) in acetonitrile/H$_2$O (9:1, 12 ml) at ambient temperature was added ceric ammonium nitrate (1.84 g) portionwise over a ten minute period. The solution was stirred overnight at room temperature. The solution was concentrated in vacuo and the resultant solid partitioned between saturated aqueous potassium carbonate (40 ml) and ethanol (60 ml). The phases were separated and the aqueous phase extracted with ethanol (4×50 ml). The ethanol portions were combined, dried over sodium sulfate and concentrated in vacuo to a tan solid. This solid was extracted exhaustively with boiling CH$_2$Cl$_2$ (10×60 ml), the organics combined, dried over sodium sulfate, filtered and concentrated to give the title compound (0.30 g) as a tan solid. $^1$H (300 MHz, DMSO-d$_6$): d 1.98 (br s, 2H), 4.08 (s, 1H), 6.86 (d, J=8.4 Hz, 1H), 7.11–7.46 (m, 8H), 10.78 (br s, 1H); $^{13}$C (75.429 MHz, DMSO-d$_6$): d 56.98, 123.41, 126.22, 126.51, 127.34, 128.30, 128.89, 130.15, 132.29, 134.42, 142.36, 168.13, 169.39. MS (FAB): m/z=268.10 (MH$^+$); TLC (CH$_2$Cl$_2$/CH$_3$OH,15:1): R$_f$=0.21

Intermediate 8

1-(2,4-Dioxo-1-phenyl-2,3,4,5-tetrahydro-1H-benzo [b] [1,4]-diazepin-3-yl)-3-phenyl urea To a slurry of 3-amino-1-phenyl-1,5-dihydro-benzo [b] [1,4]-diazepine-2,4-dione (0.398 g) in dichloromethane (5 ml) was added phenyl isocyanate (0.177 g) gradually with stirring at ambient temperature. The reaction mixture was stirred two hours at ambient temperature after which time a cream precipitate was separated by filtration to provide the title compound (0.413 g). $^1$H NMR (300 MHz, DMSO-d$_6$): d 4.97 (d, J=7.5 Hz, 1H), 6.88–6.97 (m, 3H), 7.13–7.47 (m, 12H), 9.16 (s, 1H), 10.78 (br s, 1H); TLC (CH$_2$Cl$_2$/CH$_3$OH, 19:1): R$_f$=0.21

Intermediate 9

N-isopropyl-N-phenyl-2-(2-phenylaminophenylamino)-acetamide

Potassium carbonate (6.9 g) was added to a solution of N-phenylphenylene diamine (9.2 g) in DMF and 2-bromo- N-isopropyl-N-phenyl acetamide (12.7 g) in DMF (200 ml) and the mixture was allowed to stir overnight. The DMF was evaporated in vacuo and the residue was dissolved in ethyl acetate (400 ml) and washed exhaustively with aqueous 1N HC (4×250 ml). The organic layer was washed with water (2×200 ml), dried (Na2SO4) and evaporated to give 17.8 gm of crude alkylated product. The oil was purified by chromatography on silica gel (600 g) using first $CHCl_3$ (8000 mL), then hexane:ethyl acetate (2:1, 8000 ml) as eluents to give the title compound (10 g), as an oil. $^1$H-NMR (300 MHz, $CDCl_3$): d 7.42–6.8 (m, 14 H), 6.36 (d, 1H), 4.95 (m, 1H), 3.22 (s, 2H), 1.05 (d, 6H); MS (FAB)=360 (MH$^+$); TLC, $R_f$=0.18 ($CHCl_3$).

Intermediate 10

2-[2,4-dioxo-5-phenyl-3-(phenylhydrazono)-2,3,4,5-tetrahydro benzo[b][1,4]diazepin-1-yl]-N-isopropyl-N-phenylacetamide N-isopropyl-N-phenyl-2-(2-phenylaminophenylamino)-acetamide (10 g) and 2-(phenyl-hydrazono)-propanedioyl dichloride (6.83 g), were each dissolved in THF (100 ml) and added simultaneously, with stirring, to a flask containing THF (100 ml) at 0° C., under nitrogen. The reaction mixture was allowed to warm to R.T. and stirred four hours. The THF was evaporated in vacuo and the residue was dissolved in ethyl acetate (200 ml). The ethyl acetate solution was washed with 10% aqueous sodium carbonate (2×200 ml) and water (2×200 ml), dried ($Na_2SO_4$), and concentrated in vacuo. The residual foam was treated with diethyl ether (50 ml) to precipitate the title compound as a bright yellow solid (7.5 g). The mother liquor was concentrated to a tan foam (2.5 g). $^1$H-NMR (300 MHz, $CDCl_3$): d 11.4 and 10.85 (s, 1H), 7.6–6.8 (m, 19H), 5.05 (m, 1H), 4.4 (m, 2H), 1.05 (m, 6H); MS (FAB)=532 (MH$^+$); TLC, Rf=0.19 (hexane:ethyl acetate, 2:1).

Intermediate 11

2-(3-Amino-2,4-dioxo-5-phenyl-2,3,4,5-tetrahydrobenzo-[b][1,4]diazepin-1-yl)-N-isopropyl-N-phenylacetamide Zinc powder (9.1 g) was added in portions to a slurry of 2-[2,4-dioxo-5-phenyl-3-(phenylhydrazono)-2,3,4,5-tetrahydro benzo[b][1,4]-diazepin-1-yl]-N-isopropyl-N-phenylacetamide (7.5 g), in glacial acetic acid, cooled to 0° C. The reaction was allowed to warm to R.T. and stirred an additional hour. The zinc was filtered through a celite pad and the glacial acetic acid was evaporated in vacuo. The residue was dissolved in ethyl acetate (200 ml) and washed with 10% aqueous sodium carbonate (2×100 ml) and water (2×100 ml), dried ($Na_2SO_4$) and evaporated to a tan oil. Trituration with hexane and ethyl acetate provided the title compound as a light tan powder (6.3 g). $^1$H-NMR (300 MHz, $CDCl_3$): d 7.6–6.8 (m, 14H), 5.05 (m, 1H), 4.3–4.0 (m, 3H) 1.05 (d, 6H); MS (FAB)=448 (MH$^+$); TLC, $R_f$=0.25 (chloroform:methanol, 9:1).

Intermediate 12

2-(3-Amino-2,4-dioxo-5-phenyl-2,3,4,5-tetrahydro-benzo [b] [1,4] diazepine-1-yl)-N-isopropyl-N-(4-methoxy-phenyl)-acetamide To a stirred solution of 2-[2,4-dioxo-5-phenyl-3-(phenyl-hydrazono)-2,3,4,5-tetrahydro-benzo[b][1,4]diazepine-1-yl]-N-isopropyl-N-(4-methoxy-phenyl)-acetamide (4.28 g) in acetic acid (50 mL) at ambient temperature, was added zinc dust (4.11 g) and stirred three hours. The zinc was filtered off, the filtrate concentrated in vacuo, and the resultant oil partitioned between water (60 mL) and ethyl acetate (100 mL). The pH was adjusted to 8 with 6N sodium hydroxide and the phases separated. The aqueous phase was extracted with ethyl acetate (2×75 mL) and the organics combined, dried with magnesium sulfate, filtered and concentrated in vacuo to give a yellow foam. The crude product was purified via flash chromatography on silica gel (80 g) eluted successively with ethyl acetate (260 mL) (to remove impurity) and methylene chloride/methanol (19:1, 200 ml) (to elute product). Appropriate fractions were combined and concentrated to give the title compound (2.58 g) as a yellow foam.

$^1$H (300 MHz, $CDCl_3$): d 1.08 (d, J=6.6 Hz, 6H), 2.22 (br s, 2H), 3.85 (s, 3H), 4.12–4.35 (m, 3H), 5.01 (m, 1H), 6.91–7.00 (m, 3H), 7.12 (m, 2H), 7.22–7.43 (m, 8H)

TLC ($CH_2Cl_2/CH_3OH$ (19:1)): $R_f$=0.25

Intermediate 13

2-[2,4-dioxo-5-phenyl-3-(phenyl-hydrazono)-2,3,4,5-tetrahydro-benzo[b][1,4]diazepine-1-yl]-N-isopropyl-N-(4-methoxy-phenyl)-acetamide Solutions of N-isopropyl-N-(4-methoxy-phenyl)-2-(2-phenylamino-phenylamino)-acetamide(3.00 g) in THF (30 mL) and 2-(phenyl-hydrazono) propandioyl dichloride (1.89 g) in THF (30 mL) were added concomitantly dropwise with stirring in an ice/methanol bath over a 30 minute period. After complete addition, the solution was allowed to warm to room temperature and stirred over night. The solvent was evaporated under reduced pressure and the resultant oil taken into ethyl acetate (250 mL), washed with saturated sodium bicarbonate solution, dried over sodium sulfate, filtered and concentrated under reduced pressure to give the title compound (4.28 g) as a yellow foam.

$^1$H (300 MHz, $CDCl_3$): d 1.13 (m, 6H), 3.87 (s, 3H), 4.17–4.55 (m, 2H), 5.05 (m, 1H), 6.88–7.60 (m,18H), 10.68 (s, 0.5H), 11.44 (s, 0.5H)

TLC (EtOAc/Hex (2:3)): $R_f$=0.38

Intermediate 14

N-Isopropyl-N-(4-methoxy-phenyl)-2-(2-phenylamino-phenylamino)-acetamide

To a solution of N-phenyl-benzene-1,2-diamine(3.08 g) in DMF (35 mL) was added potassium carbonate (2.31 g) and 2-bromo-N-isopropyl-N-(4-methoxy-phenyl)-acetamide (4.79 g) and stirred 18h at ambient temperature. The solvent was evaporated in vacuo and the resultant oil was dissolved in ethyl acetate(250 mL), washed with 1N HCl (4×100 mL), dried over sodium sulfate, filtered, and concentrated to a brown oil. The oil was subjected to flash chromatogaraphy on silica gel (70 g) eluted with ethyl acetate/hexanes (1:4, 1L). Fractions containing the desired product were combined and concentrated under reduced pressure to give the title compound as a tan foam (3.95 g).

$^1$H NMR (300 MHz, $CDCl_3$): d 1.05 (d, J=6.9 Hz, 6H), 3.44 (s, 2H), 3.87 (s, 3H), 4.97 (m, 1H), 5.37 (br s, 1H) 6.36 (d, J=7.4 Hz, 1H), 6.69 (t, 1H), 6.71–7.21 (m, 11H)

TLC (EtOAc/Hexane (1:4)): $R_f$=0.18

Intermediate 15

2-Bromo-N-isopropyl-N-(4-methoxy-phenyl)-acetamide

To a solution of isopropyl-(4-methoxy-phenyl)-amine (25.11 g) in dichloromethane (250 mL) was added triethylamine (15.38 g) with stirring at ambient temperature. The solution was cooled in an ice bath (<3° C.) and bromoacetyl bromide (30.68 g) dissolved in dichloromethane (100 mL) was added dropwise over a 45 minute period with stirring and cooling in an ice bath. The reaction mix was stirred overnight at ambient temperature, washed with 0.3N HCl (300 mL) and brine (300 mL), dried over sodium sulfate, filtered, and evaporated under reduced pressure to give a dark brown oil. The oil was filtered through a pad of silica gel (150 g) which was eluted with ethyl acetate/hexane (1:1, 900 mL) and the filtrate evaporated under reduced pressure to afford the title compound (41.05 g) as a brown oil which crystallized on standing.

$^1$H NMR (300 MHz, CDCl$_3$): d 1.04(d, J=6.8 Hz, 6H), 3.53(s, 2H), 3.84(s, 3H), 4.93(m, 1H), 6.93(d, J=9.1 Hz, 2H), 7.10(d, J=9.1 Hz, 3H)

TLC (EtOAc/Hexane(3:17)): R$_f$=0.18

Intermediate 16

Isopropyl-(4-methoxy-phenyl)-amine

To a stirred solution of 4-methoxy-phenylamine (1.24 g) in methanol (15 mL) at ambient temperature was added successively, glacial acetic acid (415 mg), acetone (669 mg), and 1M sodium cyanoborohydride in THF (12.7 mL). The reaction mixture was stirred overnight at room temperature. The pH was adjusted to 2 with 6N HCl and stirred for 30 minutes after which time the excess sodium cyanoborohydride was completely quenched. The pH was then adjusted to 8.5 with 1N NaOH and the resultant solution extracted with diethyl ether (2×50 mL) and ethyl acetate (50 mL). The oganic extracts were combined, dried over sodium sulfate, filtered and concentrated under reduced pressure to give the title compound (1.42 g) as a yellow oil.

$^1$H NMR (300 MHz, CDCl$_3$): d 1.18(d, J=6.1 Hz, 6H), 2.92(br s, $_1$H), 3.55(m, 1H), 3.75(s, 3H), 6.57(d, J=9.1 Hz, 2H), 6.78(d, J=8.8 Hz, 2H)

TLC (EtOAc/Hex (2:3)): R$_f$=0.72

Intermediate 17

3-Aminobenzeneacetonitrile

A solution of 3-nitrobenzeneacetonitril (8.0 g) in EtOH (100 ml) was hydrogenated at 1 atm and room temperature over 5% palladium on carbon (0.8 g) for 4 hrs. The catalyst was removed by filtration through Hyflo and the filtrate was evaporated. The residue was chromatographed, eluting with EA:Hexane (1:2) to give the title compound (5.25 g) as an orange oil.

T.l.c. hexane:EA (2:1) Rf 0.45; NMR (300 MHz, CDCl$_3$) d 3.792H,s); 3.9(2H,br); 6.7(3H,m); 7.2(H,M).

Intermediate 18

3-(2H-Tetrazol-5-yl)-phenylamine hydrochloride

3-Aminobenzonitrile (10.0 g) and tributyltinazide (42 g) were heated together at 160° C. under nitrogen for 120 minutes. The cooled mixture was diluted with ether (300 ml), extracted with 2N aqueous HCl (2×200 ml) and the combined aqueous extracts cooled in an ice-methanol bath for 30 minutes. The resulting precipitate was separated by filtration washed with ether (100 ml) and dried to give a pale pink solid. This was recrystalized from methanol (600 ml) to give the title compound as an off-white solid (12.1 g). $^1$H NMR (300 MHz, DMSO-d$_6$): d 7.32(d, J=7.8 Hz, 1H), 7.57(t, 1H), 7.82(m, 2H) m.p.: 256–262° C. (dec).

It will also be appreciated by those skilled in the art that the compounds of the present invention may also be utilized in the form of a pharmaceutically acceptable salt or solvate thereof. The physiologically acceptable salts of the compounds of Formula (I) include conventional salts formed from pharmaceutically acceptable inorganic or organic acids as well as quaternary ammonium acid addition salts. More specific examples of suitable salts include hydrochloric, hydrobromic, sulphuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts. References hereinafter to a compound according to the invention include both compounds of Formula (I) and their pharmaceutically acceptable salts and solvates.

CCK-A agonist activity of the compounds of formula (I) may be determined by standard procedures.

The relative affinities of compounds of formula (I) for the CCK-A and CCK-B receptors may also be determined using known conventional procedures such as described by Fornos et al J. Pharmacol Exp. Ther., 1992 261, 1056–1063.

The compounds of formula (I) inhibit or delay gastric emptying and thus may be used to alleviate or eliminate symptoms associated with early or prediabetes, particularly for non-insulin dependent diabetes. Such symptoms include elevated blood glucose and insulin levels, insulin resistance, increased susceptibility to infection and/or glycosuria while also maintaining gastric emptying with normal levels.

The ability of compounds of formula (I) to inhibit or delay gastric emptying may be determined using standard tests. Thus for example rats deprived for food for 18 hr were pretreated with the test compound administered i.p at a pre-set time (20 mins) before being given a methyl cellulose meal which was administered by the gavage route. The meal contains a marker element such as Phenol Red. After specific predetermined time intervals the rats are sacrificed and the amount of the meal in the stomach is determined by measuring the concentration of the marker substance present. This value is then compared with a control animal which was not pre-treated with the test compound. In this test the preferred compound of formula (I) compound 'A' when administered i.p at doses of 1 μmole/kg 20 min before gavage of test meal (1.5% methyl cellulose). completely inhibited gastric emptying 30 mins after administration of the test meal. Lower doses of the compound 'A' 0.01 and 0.1 μmoles per kg i.p also resulted in a significant reduction in gastric emptying.

According to a further aspect of the present invention, there is provided herein a method for the treatment of a mammal, including man, in particular in the treatment associated with early or prediabetes, particularly noninsulin-dependent diabetes, the method comprising administering to the patient exhibiting rapid gastric emptying an therapeutically effective amount of a compound of Formula (I) or a pharmaceutically acceptable salt or solvate thereof.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, e.g., 1–1500 mg per day. The desired dose may conveniently be presented in a single dose or as divided doses administered at appropriate intervals, for example as two, three, four or more sub-doses per day.

While it is possible that compounds of formula (I) may be therapeutically administered as the raw chemical, it is preferable to present the active ingredient as a pharmaceutical formulation. Accordingly, the present invention further provides for a pharmaceutical formulation for use in the present invention comprising a compound of Formula (I) or a pharmaceutically acceptable salt thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Formulations of the present invention include those especially formulated for oral, buccal, parenteral, implant, or rectal administration, however, oral administration is preferred. For buccal administration, the composition may take the form of tablets or lozenges formulated in conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulphate. The tablets may be coated according to methods well-known in the art. Such tablet coatings conveniently include conventional enteric coatings known to those skilled in the art e.g. cellulose acetate phthalate, polyvinyl acetate phthalate, shellac, styrene maleic acid copolymers, methyacrylic acid copolymers and hydroxypropyl methyl cellulose phthalate.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

For oral administration the compounds of formula (I) are preferably formulated as enteric coated tablets or enteric capsules.

Pharmacy

| Tablet | |
|---|---|
| Active Ingredient | 50 mg |
| Lactose anhydrous USP | 163 mg |
| Microcrystalline Cellulose NF | 69 mg |
| Pregelatinized starch Ph. Eur. | 15 mg |
| Magnesium stearate USP | 3 mg |
| Compression weight | 300 mg |

The active ingredient, microcrystalline cellulose, lactose and pregletinized starch are sieved through a 500 micron sieve and blended in a suitable mixer. The magnesium starate is sieved through a 250 micron sieve and blended with the active blend. The blend is compressed into tablets using suitable punches, then coated in a conventional manner with an enteric coating such as cellulose acetate phthalate.

I claim:

1. A method of controlling gastric emptying in patients having an early non-insulin-dependent diabetic condition and exhibiting rapid gastric emptying comprising the administration of an effective gastric emptying controlling amount of a compound of Formula (I)

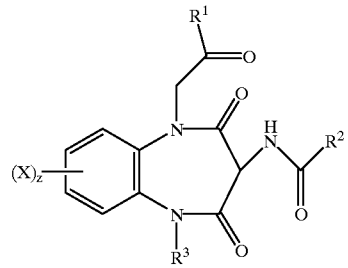

(I)

or a physiologically acceptable salt or solvate thereof wherein:

X is either hydrogen, trifluoromethyl, alkyl, $C_{1-4}$alkylthio, —O($C_{1-4}$alkyl) or halogen;

$R^1$ is either Formula II or —$NR^4R^5$;

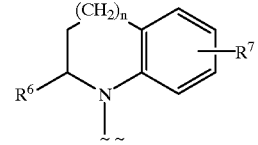

(II)

$R^2$ is either:

(1) a heterocycle linked at its 2- position and selected from pyrrole, tetrahydropyrrole, indole, benzofuran, thiophene, benzothiophene, indoline, quinoline or 4-oxobenzopyran and wherein said pyrrole, tetrahydropyrrole, indole or indoline may optionally be substituted on the ring nitrogen thereof by the group $R^8$ as defined hereunder and said indole, indoline, quinoline, benzofuran, benzothiophene or 4-oxo-benzopyran may optionally be substituted in the benzo ring thereof by the group $R^9$ as defined hereunder or (2) phenyl or phenyl mono- or disubstituted independently with halogen, hydroxy, cyano, carboxy, —O($C_{1-4}$alkyl), —O($CH_2C_6H_5$), —COO($C_{1-4}$alkyl), amino, dimethylamino, —$NHR^{10}$, 1-pyrrolidinyl or tetrazolyl; or (3) pyridine or pyridinyl mono- or disubstituted independently with halogen, methyl, hydroxy, nitro, cyano, carboxy, —O($C_{1-4}$alkyl), —O($CH_2C_6H_5$), —COO($C_{1-4}$alkyl), amino or dimethylamino; or (4) —$NHR^{11}$ where $R^{11}$ is defined hereinunder or $R^{11}$ is 7-indazolyl containing a group $R^{10}$ at the N–1 position;

$R^3$ is hydrogen, $C_{1-6}$alkyl, $C_{3-6}$cycloalkyl, phenyl or phenyl mono- or disubstituted independently with halogen;

$R^4$ is independently $C_{3-6}$alkyl, $C_{3-6}$cycloalkyl, $C_{3-6}$alkenyl, phenyl, —$(CH_2)_pCN$ or —$(CH_2)_pCOO$($C_{1-4}$alkyl) and $R^5$ is independently $C_{3-6}$alkyl, $C_{3-6}$cycloalkyl, $C_{3-6}$ alkenyl, benzyl, phenyl or phenyl mono- or disubstituted independently with $C_{1-3}$alkyl, cyano, hydroxy, dimethylamino, —O($C_{1-4}$alkyl), —O($CH_2C_6H_5$), —NH($C_{1-4}$alkyl), —COO($C_{1-4}$alkyl), —N($C_{1-4}$alkyl)$_2$ pyrrolidino, morpholino or halogen or $R^4$ is $C_{1-2}$alkyl and $R^5$ is phenyl substituted at the 2- or 4-position with chloro, methyl, methoxy or methoxycarbonyl;

$R^6$ is hydrogen or methyl;

$R^7$ is hydrogen, hydroxy, fluoro, dimethylamino, —O($C_{1-4}$alkyl) or —O($CH_2C_6H_5$);

$R^8$ is —$(CH_2)_bCOOH$;

$R^9$ is methyl, chloro, nitro, hydroxy, methoxy or —$NHR^{10}$;

$R^{10}$ is hydrogen, acetyl, $C_{1-4}$alkyl, —$SO_3H$, —$SO_2CH_3$, —$SO_2CF_3$ or —$SO_2C_6H_5$, $C_{1-4}$alkoxycarbonyl;

$R^{11}$ is phenyl or phenyl mono- or disubstituted independently with fluorine, trifluoromethoxy, $C_{1-4}$alkylthio, —$(CH_2)_cCOOH$, —$(CH_2)_cCOO(C_{1-4}$alkyl), —$(CH_2)_cSCH_3$, —$(CH_2)_cSOCH_3$, —$(CH_2)_cSO_2CH_3$, —$(CH_2)_cCONH_2$, —$SCH_2COOH$, —$CONH(SO_2CH_3)$, —$CONH(SO_2CF_3)$, —$(CH_2)_cN(C_{1-4}$alkyl)$_2$, —$(CH_2)_cNH(SO_2CF_3)$, —$(CH_2)_cN(SO_2CF_3)(C_{1-4}$alkyl), —$(CH_2)_cSO_2NHCO(C_{1-4}$alkyl), —$(CH_2)_cSO_2N(C_{1-4}$alkyl)CO($C_{1-4}$alkyl), —$(CH_2)_cCONHSO_2$($C_{1-4}$alkyl), —$(CH_2)_cCON(C_{1-4}$alkyl)$SO_2$($C_{1-4}$alkyl), —$(CH_2)_cOR^{12}$ —$(CH_2)_cNHR^{10}$ or phenyl monosubstituted with —$(CH_2)_c$(tetrazolyl), —$(CH_2)_c$(carboxamidotetrazolyl) or —$(CH_2)_c$(pyrrolidinyl) or $R^{11}$ is selected from pyridine or pyridinyl mono- or disubstituted independently with halogen, methyl, hydroxy, nitro, cyano, carboxy, —O($C_{1-4}$ alkyl), amino, dimethylamino, —$NHR^{10}$;

$R^{12}$ is hydrogen, $C_{1-6}$alkyl, $C_{3-6}$cycloalkyl, —$CH_2C_6H_5$, —$CH_2COOH$, —$CH_2CONH_2$, —$CH_2CONH$($C_{1-4}$alkyl), —$CH_2CON(C_{1-4}$alkyl)$_2$ or

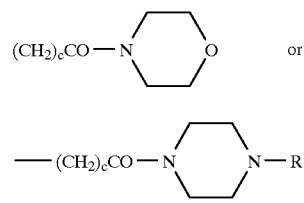

z is 1 or 2;
n is 1 or 2;

p is an integer from 1–4;
b is an integer from 0–3; and
c is 0 or 1.

2. The method of claim 1 wherein $R^1$ represents the group of Formula (II) wherein $R^6$ is methyl, $R^7$ is hydrogen, hydroxyl, methoxy or fluorine and n is 1 or $R^1$ represents the group $NR^4R^5$ wherein $R^4$ represents $C_{3-6}$ alkyl, cyclohexyl or phenyl, and $R^5$ represents $C_{3-6}$ alkyl or phenyl optionally substituted in the para position by hydroxy, dimethylamino, methoxy, fluorine, pyrrolidino or morpholino.

3. The method of claim 1 wherein $R^1$ represents the group $NR^4R^5$ and $R^4$ represents propyl or isopropyl and $R^5$ represents phenyl or phenyl substituted in the para position by a group selected from hydroxy, methoxy, dimethylamino, fluorine, or morpholino.

4. The method of claim 1 wherein $R^2$ represents a group selected from phenyl (optionally substituted by one or two groups which may be the same or different and selected from chlorine, fluorine, amino, hydroxy or carboxy,) or $NHR^{11}$ wherein $R^{11}$ is phenyl (optionally substituted by fluoro, hydroxy, amino, dimethylamino, trifluoromethylsulphonylamino, $C_{1-4}$ alkoxycarbonyl, carboxy, 1H-tetrazol-5-yl, acetylamino or $OR^{12}$ wherein $R^{12}$ represents hydrogen, methyl, benzyl, $CH_2CO_2H$, $CH_2CONH_2$, $CH_2CONHCH_3$, $CH_2CON(CH_3)_2$

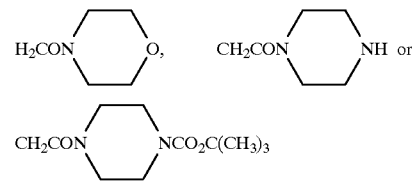

or 7-indazolyl wherein the N–1 substituted is hydrogen, or $R^2$ represents an indole group wherein the nitrogen atom is optionally substituted by the group —$CH_2CO_2H$ and the benzo ring is optionally substituted by a group selected from chlorine, methyl, methoxy, nitro, hydroxy or amino.

5. The method of claim 1 wherein $R^2$ represents an indole group which is unsubstituted on the nitrogen atom and in which the benzo ring thereof is optionally substituted by a group selected from chlorine, methyl, methoxy, nitro, hydroxy or amino.

6. The method of claim 1 wherein $R^3$ represents hydrogen, methyl, cyclohexyl,2-fluorophenyl or phenyl.

7. The method of claim 1 wherein $R^3$ represents phenyl.

8. The method of claim 1 wherein X represents hydrogen.

9. The method of claim 1 wherein $R^1$ represents $NR^4R^5$ and $R^4$ represents isopropyl and $R^5$ represents p-methoxyphenyl; $R^2$ represents an unsubstituted 2-indole group; $R^3$ represents phenyl and X represents hydrogen and enantiomers thereof.

10. A method of controlling gastric emptying in patients having an early non-insulin-dependent diabetic condition and exhibiting rapid gastric emptying comprising the administration of an effective gastric emptying controlling amount of 1H-Indole-2-carboxylic acid {1-[isopropyl-(4-methoxyphenyl)carbamoyl-methyl]-2,4-dioxo-5-phenyl-2,3,4,5-tetrahydro-1H-benzo[b][1,4]diazepin-3-yl}amide or enantiomers thereof or pharmaceutically acceptable salts or solvates thereof.

* * * * *